United States Patent
Braun et al.

(10) Patent No.: US 9,107,414 B2
(45) Date of Patent: Aug. 18, 2015

(54) TETRAZOL-5-YL- AND TRIAZOL-5-YL-ARYL COMPOUNDS AND USE THEREOF AS HERBICIDES

(71) Applicant: BAYER INTELLECTUAL PROPERTY GMBH, Monheim (DE)

(72) Inventors: Ralf Braun, Ramberg (DE); Lothar Willms, Hofheim am Taunus (DE); Ines Heinemann, Hofheim am Taunus (DE); Isolde Haeuser-Hahn, Leverkusen (DE); Hansjoerg Dietrich, Liederbach (DE); Elmar Gatzweiler, Bad Nauheim (DE); Christopher Hugh Rosinger, Hofheim am Taunus (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/370,309

(22) PCT Filed: Jan. 10, 2013

(86) PCT No.: PCT/EP2013/050383
§ 371 (c)(1),
(2) Date: Jul. 2, 2014

(87) PCT Pub. No.: WO2013/104705
PCT Pub. Date: Jul. 18, 2013

(65) Prior Publication Data
US 2014/0342906 A1    Nov. 20, 2014

(30) Foreign Application Priority Data
Jan. 11, 2012  (EP) .................................... 12150731

(51) Int. Cl.
| | |
|---|---|
| C07D 249/08 | (2006.01) |
| C07D 261/18 | (2006.01) |
| C07D 257/00 | (2006.01) |
| A01N 43/653 | (2006.01) |
| A01N 43/713 | (2006.01) |
| C07D 403/06 | (2006.01) |
| C07D 405/12 | (2006.01) |
| C07D 413/10 | (2006.01) |
| C07D 257/04 | (2006.01) |
| A01N 43/80 | (2006.01) |
| A01N 25/32 | (2006.01) |
| C07D 401/10 | (2006.01) |
| C07D 403/10 | (2006.01) |

(52) U.S. Cl.
CPC ............. *A01N 43/653* (2013.01); *A01N 25/32* (2013.01); *A01N 43/713* (2013.01); *A01N 43/80* (2013.01); *C07D 249/08* (2013.01); *C07D 257/04* (2013.01); *C07D 401/10* (2013.01); *C07D 403/06* (2013.01); *C07D 403/10* (2013.01); *C07D 405/12* (2013.01); *C07D 413/10* (2013.01)

(58) Field of Classification Search
CPC ....................................................... C07D 249/08
USPC ......... 548/267.4, 266.2, 247, 253; 546/268.4, 546/272.4
See application file for complete search history.

(56) References Cited

U.S. PATENT DOCUMENTS 6,063,734 A * 5/2000 Ogura et al. ................... 504/261
6,462,049 B1 * 10/2002 Ogura et al. ............. 514/254.02

FOREIGN PATENT DOCUMENTS

| DE | 294258 A5 | 9/1991 |
| EP | 00206523 A1 | 12/1986 |
| JP | WO 9902507 * | 1/1999 |
| WO | 9902507 A1 | 1/1999 |
| WO | 2005030736 A1 | 4/2005 |

OTHER PUBLICATIONS

International Search Report received in PCT/EP2013/050383, mailed Mar. 6, 2013.
G.W. Fischer, Tetrazolverbindungen. 7 [1], Chem. Bd. 336, Nr. 1, 1994, S. 79-82, XP002678978.

* cited by examiner

*Primary Examiner* — Nizal Chandrakumar
(74) *Attorney, Agent, or Firm* — Miles & Stockbridge P.C.

(57) ABSTRACT

Tetrazol-5-yl- and triazol-5-yl-aryl compounds of the general formula (I) as herbicides are described.

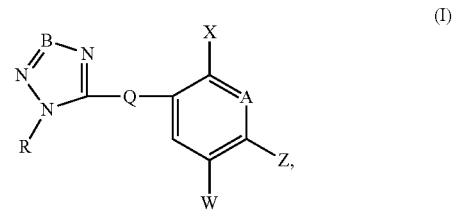

In this formula (I), X, Z, W and R are radicals such as hydrogen, organic radicals such as alkyl, and other radicals such as halogen. A and B are N and CY. Q is cyanoalkylcarbonyl or isoxazolyl.

20 Claims, No Drawings

TETRAZOL-5-YL- AND TRIAZOL-5-YL-ARYL COMPOUNDS AND USE THEREOF AS HERBICIDES

CROSS REFERENCE TO RELATED APPLICATIONS

This application is a §371 National Stage Application of PCT/EP2013/050383, filed Jan. 10, 2013, which claims priority to EP 12150731.3, filed Jan. 11, 2012.

BACKGROUND

1. Field of the Invention

The invention relates to the technical field of herbicides, especially that of herbicides for the selective control of broad-leaved weeds and weed grasses in crops of useful plants.

2. Description of Related Art

WO 2005030736 A1 discloses 1-benzoyl-1-(tetrazol-5-yl)-2-oxopropanes as herbicides. European patent application EP 10174893, which has an earlier priority date but was yet to be published before the priority date of the present application, discloses particular N-(tetrazol-5-yl)- and N-(triazol-5-yl)benzamides and -nicotinamides as herbicides.

However, frequently, the compounds known from this publication have insufficient herbicidal activity or an insufficient compatibility with crop plants. Accordingly, it is an object of the present invention to provide further herbicidally active compounds. It has now been found that certain tetrazol-5-yl- and triazol-5-yl-aryl derivatives are of particularly good suitability as herbicides.

SUMMARY

The present invention provides tetrazol-5-yl and triazol-5-yl-aryl compounds of the formula (I) or salts thereof

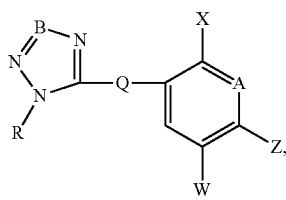
(I)

in which
Q is $Q^1$ or $Q^2$

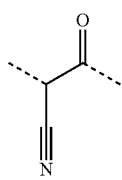
$Q^1$

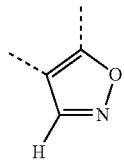
$Q^2$ where in each case the oxygen-carrying carbon atom is bonded to the aryl moiety of the compound of the formula (I),
A is N or CY,
B is N or CH,
X is nitro, halogen, cyano, formyl, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $NR_1R_2$, $P(O)(OR^5)_2$, $CH_2P(O)(OR^5)_2$, $(C_1\text{-}C_6)$-alkylheteroaryl, $(C_1\text{-}C_6)$-alkylheterocyclyl, where the two last-mentioned radicals are each substituted by s radicals from the group consisting of halogen, $(C_1\text{-}C_6)$-alkyl, halo-$(C_1\text{-}C_6)$-alkyl, $S(O)_n\text{---}(C_1\text{-}C_6)$-alkyl, $(C_1\text{-}C_6)$-alkoxy and halo-$(C_1\text{-}C_6)$-alkoxy, and where heterocyclyl carries n oxo groups,
Y is hydrogen, nitro, halogen, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, $(C_3\text{-}C_6)$-cycloalkenyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO2R^2$, $(C_1\text{-}C_6)$-alkyl-$CO_2R^1$, $(C_1\text{-}C_6)$-alkyl-CN, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $N(R^1)_2$, $P(O)(OR^5)_2$, $CH_2P(O)(OR^5)_2$, $(C_1\text{-}C_6)$-alkylphenyl, $(C_1\text{-}C_6)$-alkylheteroaryl, $(C_1\text{-}C_6)$-alkylheterocyclyl, phenyl, heteroaryl or heterocyclyl, where the 6 last-mentioned radicals are each substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $S(O)_n\text{---}(C_1\text{-}C_6)$-alkyl, $(C_1\text{-}C_6)$-alkoxy, halo-$(C_1\text{-}C_6)$-alkoxy, $(C_1\text{-}C_6)$-alkoxy-$(C_1\text{-}C_4)$-alkyl and cyanomethyl, and where heterocyclyl carries n oxo groups,
Z is halogen, cyano, thiocyanato, nitro, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $N(R^1)_2$, $P(O)(OR^5)_2$, heteroaryl, heterocyclyl or phenyl, where the three last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy and halo-$(C_1-C_6)$-alkoxy, and where heterocyclyl carries n oxo groups, Z may also be hydrogen, $(C_1-C_6)$-alkyl or $(C_1-C_6)$-alkoxy if Y is the $S(O)_nR^2$ radical, W is hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, $(C_3-C_7)$-halocycloalkyl, $(C_1-C_6)$-alkoxy, $(C_1-C_6)$-haloalkoxy, $S(O)_n$—$(C_1-C_6)$-alkyl, $S(O)_n$—$(C_1-C_6)$-haloalkyl, $(C_1-C_6)$-alkoxy-$(C_1-C_4)$-alkyl, $(C_1-C_6)$-alkoxy-$(C_1-C_4)$-haloalkyl, halogen, nitro, $NR^3COR^3$ or cyano, R is $(C_1-C_8)$-alkyl, halo-$(C_1-C_6)$-alkyl, $(C_2-C_8)$-alkenyl, halo-$(C_2-C_8)$-alkenyl, $(C_2-C_8)$-alkynyl, halo-$(C_2-C_8)$-alkynyl or $(C_3-C_7)$-cycloalkylmethyl, where these seven aforementioned radicals are each substituted by s radicals form the group consisting of hydroxy, nitro, cyano, $SiR^5_3$, $PO(OR^5)_2$, $S(O)_n$—$(C_1-C_6)$-alkyl, $S(O)_n$—$(C_1-C_6)$-haloalkyl, $(C_1-C_6)$-alkoxy, halo-$(C_1-C_6)$-alkoxy, $N(R^3)_2$, $COR^3$, $COOR^3$, $OCOR^3$, $NR^3COR^3$, $NR^3SO_2R^4$, $O(C_1-C_2)$-alkyl-$(C_3-C_6)$-cycloalkyl, $(C_3-C_6)$-cycloalkyl, heteroaryl, heterocyclyl and phenyl, where the three last-mentioned radicals are each substituted by s radicals from the group consisting of methyl, ethyl, methoxy, trifluoromethyl, cyano and halogen, and where heterocyclyl carries n oxo groups, or R is $(C_3-C_7)$-cycloalkyl, heteroaryl, heterocyclyl or phenyl, where these four aforementioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, and where heterocyclyl carries n oxo groups, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 last-mentioned radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries n oxo groups, $R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 last-mentioned radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl carries n oxo groups, $R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ is $(C_1-C_6)$-alkyl, $(C_2-C_6)$-alkenyl or $(C_2-C_6)$-alkynyl, $R^5$ is methyl or ethyl, n is 0, 1 or 2, s is 0, 1, 2 or 3.

DETAILED DESCRIPTION OF A PREFERRED EMBODIMENT

In the formula (I) and all the formulae which follow, alkyl radicals having more than two carbon atoms may be straight-chain or branched. Alkyl radicals are for example methyl, ethyl, n- or i-propyl, n-, i-, t- or 2-butyl, pentyls, hexyls, such as n-hexyl, i-hexyl and 1,3-dimethylbutyl. Analogously, alkenyl is for example allyl, 1-methylprop-2-en-1-yl, 2-methylprop-2-en-1-yl, but-2-en-1-yl, but-3-en-1-yl, 1-methyl-but-3-en-1-yl and 1-methyl-but-2-en-1-yl. Alkynyl is for example propargyl, but-2-yn-1-yl, but-3-yn-1-yl, 1-methyl-but-3-yn-1-yl. The multiple bond may be in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl. When a group is polysubstituted by radicals, this means that this group is substituted by one or more identical or different radicals from those mentioned.

Depending on the nature and the attachment of the substituents, the compounds of the general formula (I) may be present as stereoisomers. When, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is equally possible to selectively prepare stereoisomers by using stereoselective reactions using optically active starting materials and/or auxiliaries. The invention also relates to all stereoisomers and mixtures thereof which are encompassed by the general formula (I) but not defined specifically.

Preference is given to compounds of the general formula (I) in which
Q is $Q^1$ or $Q^2$,
A is N or CY,
B is N or CH,
X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_1-C_6)$-alkyl-O—$(C_1-C_6)$-alkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$ or $(C_1-C_6)$-alkyl-$NR^1SO_2R^2$, $(C_1-C_6)$-alkylheteroaryl, $(C_1-C_6)$-alkylheterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $COOR^1$, $OSO_2R^2$, $S(O)_nR^2$, $SO_2OR^1$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups,
Z is halogen, cyano, thiocyanato, nitro, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $C(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$ or 1,2,4-triazol-1-yl, or
Z may also be hydrogen, $(C_1-C_6)$-alkyl or $(C_1-C_6)$-alkoxy if Y is the $S(O)_nR^2$ radical,
W is hydrogen, $(C_1-C_6)$-alkyl, halo-$(C_1-C_6)$-alkyl, $(C_1-C_6)$-alkoxy, $(C_1-C_6)$-haloalkoxy, $S(O)_n$—$(C_1-C_6)$-alkyl, $S(O)_n$—$(C_1-C_6)$-haloalkyl, $(C_1-C_6)$-alkoxy-$(C_1-C_4)$-alkyl, halogen, nitro or cyano,
R is $(C_1-C_6)$-alkyl, halo-$(C_1-C_6)$-alkyl, $(C_2-C_8)$-alkenyl, halo-$(C_2-C_6)$-alkenyl, $(C_2-C_8)$-alkynyl, halo-$(C_2-C_6)$-alkynyl or $(C_3-C_7)$-cycloalkylmethyl, where these seven aforementioned radicals are each substituted by s radicals from the group consisting of the group cyano, $S(O)_n$—$(C_1-C_6)$-alkyl, $S(O)_n$—$(C_1-C_6)$-haloalkyl, $(C_1-C_6)$-alkoxy and halo-$(C_1-C_6)$-alkoxy, $R^1$ is hydrogen, $(C_1-C_6)$-alkyl, $(C_2-C_6)$-alkenyl, $(C_2-C_6)$-alkynyl, $(C_3-C_6)$-cycloalkyl, (03-06)-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 latter radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl bears n oxo groups,
$R^2$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C1-C_6)$-alkyl-O-heterocyclyl, $(C_1-C_6)$-alkyl-$NR^3$-heteroaryl or $(C_1-C_6)$-alkyl-$NR^3$-heterocyclyl, where 15 last-mentioned radicals are each substituted s radicals from the group consisting of cyano, halogen, nitro, $OR^3$, $S(O)_nR^4$, $N(R^3)_2$, $NR^3OR^3$, $NR^3SO_2R^4$, $COR^3$, $OCOR^3$, $NR^3COR^3$, $CO_2R^3$, $CON(R^3)_2$ and $(C_1-C_4)$-alkoxy-$(C_2-C_6)$-alkoxycarbonyl, and where heterocyclyl carries n oxo groups,
$R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl,
$R^4$ is $(C_1-C_6)$-alkyl, $(C_2-C_6)$-alkenyl or $(C_2-C_6)$-alkynyl,
n is 0, 1 or 2,
s is 0, 1, 2 or 3.
Particular preference is given to compounds of the general formula (I) in which
Q is $Q^1$ or $Q^2$,
A is N or CY,
B is N or CH,
is nitro, halogen, cyano, $(C_1-C_6)$-alkyl, halo-$(C_1-C_6)$-alkyl, $(C_3-C_6)$-cycloalkyl, $OR^1$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-heteroaryl or $(C_1-C_6)$-alkylheterocyclyl, where the two last-mentioned radicals are substituted in each case by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups,
Y is hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 last-mentioned radicals are each substituted by s radicals from the group halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups,
Z is halogen, cyano, nitro, halo-$(C_1-C_6)$-alkyl, $(C_3-C_6)$-cycloalkyl, $S(O)_nR^2$ or 1,2,4-triazol-1-yl, or else Z may be hydrogen, methyl, methoxy or ethoxy if Y is the radical $S(O)_nR^2$,
W is hydrogen, methyl, ethyl, fluorine, chlorine or $S(O)_nCH_3$,
R is $(C_1-C_8)$-alkyl, halo-$(C_1-C_6)$-alkyl, $(C_2-C_8)$-alkenyl, halo-$(C—C_6)$-alkenyl, $(C_2-C_8)$-alkynyl, halo-$(C_2-C_6)$-alkynyl or $(C_3-C_7)$-cycloalkylmethyl, where these seven radicals are each substituted by s radicals from the group consisting of cyano, $S(O)_n$—$(C_1$-$C_6)$-alkyl, $S(O)_n$—$(C_1$-$C_6)$-haloalkyl, $(C_1$-$C_6)$-alkoxy and halo-$(C_1$-$C_6)$-alkoxy, $R^1$ is hydrogen, $(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkyl-$(C_1$-$C_6)$-alkyl, $(C_1$-$C_6)$-alkyl-O—$(C_1$-$C_6)$-alkyl, phenyl, phenyl-$(C_1$-$C_6)$-alkyl, heteroaryl, $(C_1$-$C_6)$-alkylheteroaryl, heterocyclyl, $(C_1$-$C_6)$-alkylheterocyclyl, $(C_1$-$C_6)$-alkyl-O-heteroaryl, $(C_1$-$C_6)$-alkyl-O-heterocyclyl, $(C_1$-$C_6)$-alkyl-$NR^3$-heteroaryl or $(C_1$-$C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1$-$C_4)$-alkoxy-$(C_2$-$C_6)$-alkoxycarbonyl, and where heterocyclyl carries n oxo groups, $R^2$ is $(C_1$-$C_6)$-alkyl, $(C_3$-$C_6)$-cycloalkyl or $(C_3$-$C_6)$-cycloalkyl-$(C_1$-$C_6)$-alkyl, where these three aforementioned radicals are each substituted by s radicals from the group consisting of halogen and $OR^3$, $R^3$ is hydrogen or $(C_1$-$C_6)$-alkyl, $R^4$ is $(C_1$-$C_6)$-alkyl, n is 0, 1 or 2, s is 0, 1, 2 or 3.

In all the formulae specified hereinafter, the substituents and symbols have the same meaning as in formula (I), unless defined differently.

Compound (I-$Q^1$) according to the invention can be prepared, for example, by the method shown in scheme 1 by reacting an isoxazole (I-$Q^2$) with a base, where the salt produced can be converted to the neutral end compound by reaction with an acid.

Compound (I-$Q^1$) according to the invention can also be prepared, for example, by the method shown in scheme 2, by base-catalyzed reaction of an aroyl chloride (II) with a 5-cyanomethy-1-H-1,2,4-triazole or 5-cyanomethyl-1H-tetrazole (III):

The benzoyl chlorides of the formula (II) or the parent benzoic acids thereof (IV) are known in principle and can be prepared, for example, by the methods described in U.S. Pat. No. 6,376,429 B1, EP 1 585 742 A1 and EP 1 202 978 A1.

Compounds (I-$Q^1$) according to the invention can also be prepared by the method shown in scheme 3, by reacting a benzoic acid of the formula (IV) with a 5-cyanomethy-1-H-1,2,4-triazole or 5-cyanomethyl-1H-tetrazole (III):

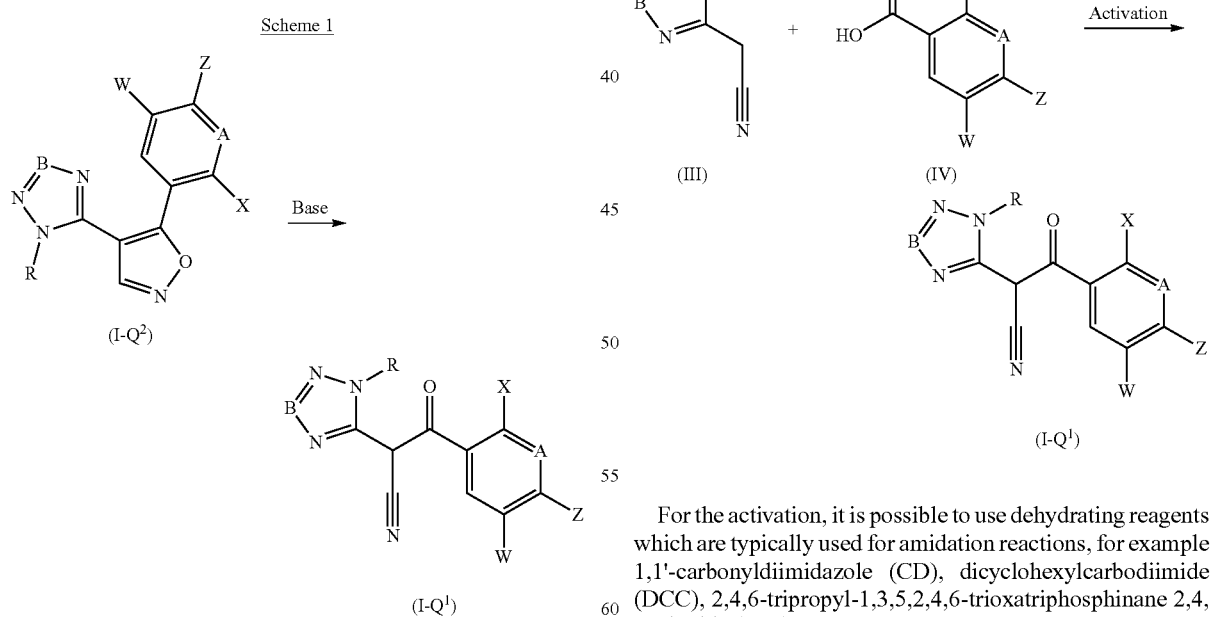

For the activation, it is possible to use dehydrating reagents which are typically used for amidation reactions, for example 1,1'-carbonyldiimidazole (CD), dicyclohexylcarbodiimide (DCC), 2,4,6-tripropyl-1,3,5,2,4,6-trioxatriphosphinane 2,4,6-trioxide (T3P) etc.

Compounds (I-$Q^1$) according to the invention where B═N can also be prepared by the method shown in scheme 4 by reacting a 2-aroyl-3-aminoalkyl-3-thioalkylacrylonitrile with an azide analogously to the method described in Zeitschrift für Naturforschung, B: Chemical Sciences (1996), 51(3), 399-408:

Scheme 4

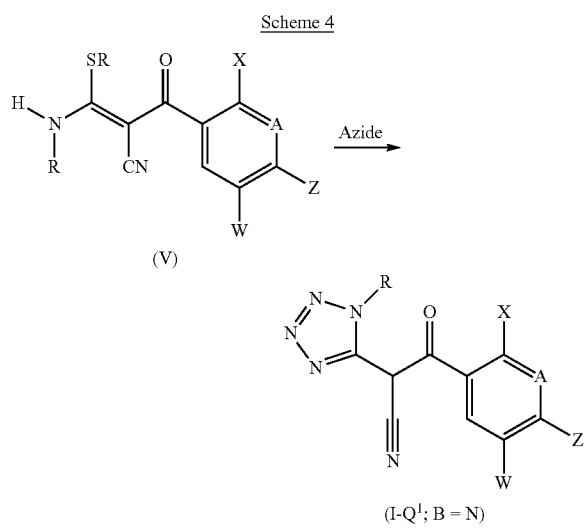

For this reaction specified in scheme 4, azide sources such as e.g. sodium azide can be used.

It may be appropriate to alter the sequence of reaction steps. For instance, benzoic acids bearing a sulfoxide cannot be converted directly to their acid chlorides. Here, it is advisable to prepare initially, at the thioether stage, the amide and then to oxidize the thioether to the sulfoxide.

Compounds of the structure (V) can be prepared according to scheme 5 for example analogously to the methods described in WO 200994224 A1 and EP 286 153 B1:

Scheme 5

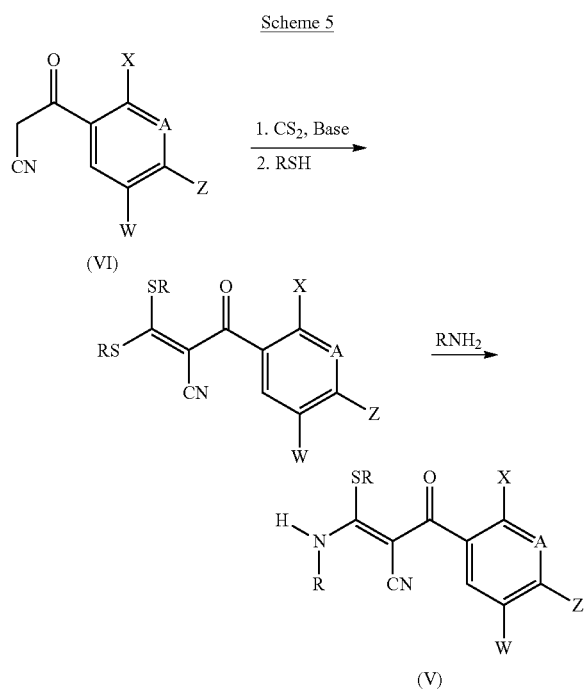

Compounds of the structure (V) can alternatively also be prepared according to scheme 6 for example analogously to the methods described in Chemische Berichte (1968), 101(3), 1131-1133:

Scheme 6

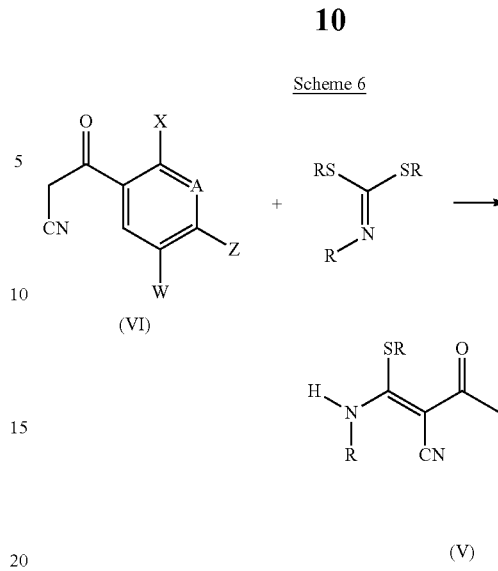

Isoxazoles of the structure (I-$Q^2$) can be prepared according to scheme 7, where the first step can be carried out analogously to the method described in Journal of Heterocyclic Chemistry (1986), 23(4), 1257-62, the second analogously to U.S. Pat. No. 4,659,718, the last two for example analogously to the method described in WO 2011012248.

Scheme 7

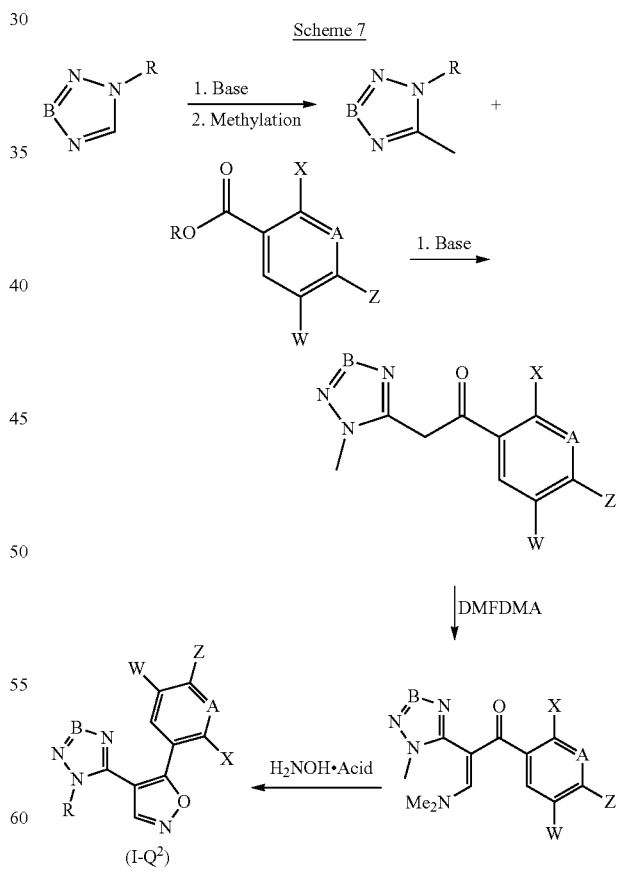

The aroylacetonitriles can be prepared for example according to scheme 8 analogously to the procedure described in Bioorganic & Medicinal Chemistry Letters (2006), 16(7), 1924-1928 from the benzoic acids and cyanoacetate:

Scheme 8

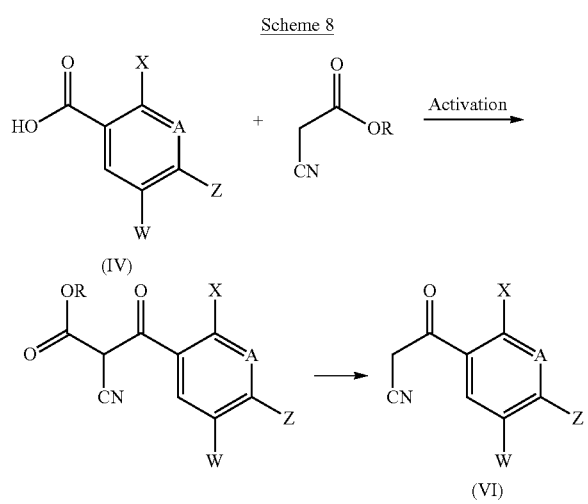

5-Cyanomethy-1-H-1,2,4-triazole or 5-cyanomethyl-1H-tetrazole (111) can be prepared for example according to scheme 9, where the first step can be carried out analogously to the method described in WO 201025407 A1, the second analogously to Journal of Antibiotics (1993), 46(12), 1866-1882, the last analogously to the method described in US200369257.

Scheme 9

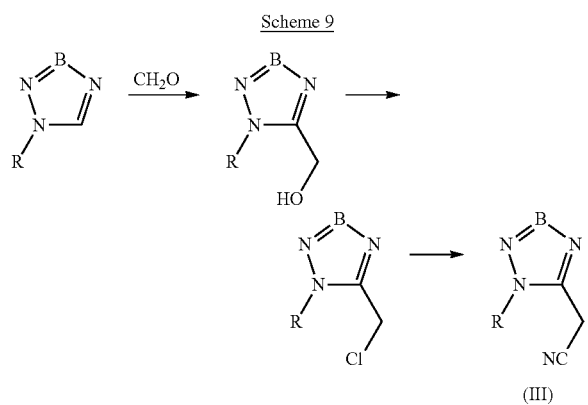

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry Synthesis, Analysis, Screening (editor: Günther Jung), Wiley, 1999. The use of solid phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editor C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds according to the invention of the formula (I) (and/or salts thereof), collectively referred to hereinafter as "compounds according to the invention", have excellent herbicidal efficacy against a broad spectrum of economically important monocotyledonous and dicotyledonous annual weed plants. Perennial weed plants which are difficult to control and produce shoots from rhizomes, root stocks or other perennial organs are also readily controlled by the active ingredients.

The present invention therefore also provides a method for controlling unwanted plants or for regulating the growth of plants, preferably in plant crops, in which one or more compound(s) according to the invention is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples of some representatives of the monocotyledonous and dicotyledonous weed flora which can be controlled by the compounds according to the invention are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the weed seedlings are prevented completely from emerging or the weeds grow until they have reached the cotyledon stage, but then stop growing and, eventually, after three to four weeks have passed, die completely.

If the active ingredients are applied post-emergence to the green parts of the plants, there is likewise stoppage of growth after the treatment, and the weed plants remain at the growth stage of the time of application, or they die completely after a certain time, such that competition by the weeds, which is harmful to the crop plants, is thus eliminated very early and in a lasting manner.

Although the compounds according to the invention have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* especially *Zea* and *Triticum,* are damaged only to an insignificant extent, if at all, depending on the structure of the respective compound according to the invention and the application rate thereof. For these reasons, the present compounds are very suitable for the selective control of unwanted plant growth in plant crops such as agriculturally useful plants or ornamentals.

In addition, the compounds according to the invention (depending on their particular structure and the application rate deployed) have outstanding growth-regulating properties in crop plants. They intervene in the plant's own metabolism with a regulatory effect, and can thus be used to control plant constituents and to facilitate harvesting, for example by triggering desiccation and stunted growth. In addition, they are also suitable for the general control and inhibition of unwanted vegetative growth without killing the plants. Inhibiting vegetative growth plays a major role for many monocotyledonous and dicotyledonous crops, since, for example, this can reduce or completely prevent lodging.

By virtue of their herbicidal and plant-growth-regulating properties, the active ingredients can also be used for controlling harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferred, with respect to transgenic crops, to use the compounds according to the invention in economically important transgenic crops of useful plants and ornamentals, for example of cereals such as wheat, barley, rye, oats, milletsorghum, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Preference is given to the use of the compounds according to the invention or salts thereof in economically important transgenic crops of useful plants and ornamentals, for example of cereals such as wheat, barley, rye, oats, milletsorghum, rice, cassava and corn, or else crops of sugar beet, cotton, soybean, oilseed rape, potato, tomato, peas and other vegetables. Preferably, the compounds according to the invention can be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

recombinant modifications of crop plants for the purpose of modifying the starch synthesized in the plants (e.g. WO 9211376, WO 9214827, WO 9119806), transgenic crop plants which are resistant to particular herbicides of the glufosinate type (cf., for example, EP-A-0242236, EP-A-242246) or glyphosate type (WO 9200377) or of the sulfonylurea type (EP-A-0257993, U.S. Pat. No. 5,013,659), transgenic crop plants, for example cotton, with the ability to produce *Bacillus thuringiensis* toxins (Bt toxins) which make the plants resistant to particular pests (EP-A-0142924, EP-A-0193259), transgenic crop plants with a modified fatty acid composition (WO 9113972), genetically modified crop plants with novel constituents or secondary metabolites, for example novel phytoalexins, which cause an increased disease resistance (EPA 309862, EPA 0464461), genetically modified plants with reduced photorespiration, which have higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are notable for a combination, for example, of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product. To this end, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

For instance, it is possible to obtain transgenic plants whose properties are altered by overexpression, suppression or inhibition of homologous (=natural) genes or gene sequences, or expression of heterologous (=foreign) genes or gene sequences.

Preferably, the compounds according to the invention can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the active ingredients according to the invention in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds according to the invention as herbicides for control of weed plants in transgenic crop plants.

The compounds according to the invention can be applied in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Engineering], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Engineering], volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are ground finely, for example in customary apparatuses such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may be, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active ingredient onto granulated inert material capable of adsorption or by applying active ingredient concentrates to the surface of carrier substances, such as sand, kaolinites or granulated inert material, by means of adhesives, for example polyvinyl alcohol, sodium polyacrylate or mineral oils. Suitable active ingredients can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical preparations contain generally from 0.1 to 99% by weight, in particular from 0.1 to 95% by weight, of compounds according to the invention. In wettable powders, the active ingredient concentration is, for example, about 10 to 90% by weight, the remainder to 100% consisting of customary formulation constituents. In emulsifiable concentrates, the active ingredient concentration may be about 1 to 90% and preferably 5 to 80% by weight. Formulations in the form of dusts comprise 1 to 30% by weight of active ingredient, preferably usually 5 to 20% by weight of active ingredient; sprayable solutions contain about 0.05 to 80, preferably 2 to 50, % by weight of active ingredient. In the case of water-dispersible granules, the active ingredient content depends partially on whether the active compound is present in liquid or solid form and on which granulation auxiliaries, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active substances, such as, for example, insecticides, acaricides, herbicides, fungicides, and also with safeners, fertilizers and/or growth regulators, for example in the form of a finished formulation or as a tank mix.

Active ingredients which can be employed in combination with the compounds according to the invention in mixed formulations or in the tank mix are, for example, known active ingredients which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2009 and the literature cited therein. Examples of known herbicides or plant growth regulators which can be combined with the compounds according to the invention include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. One administration form or else, in some cases, more than one administration form is mentioned by way of example:
acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimurondymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. 0-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6- dimethoxypyrimidin-2-yl)oxy]benzyl}aniline, and the following compounds:

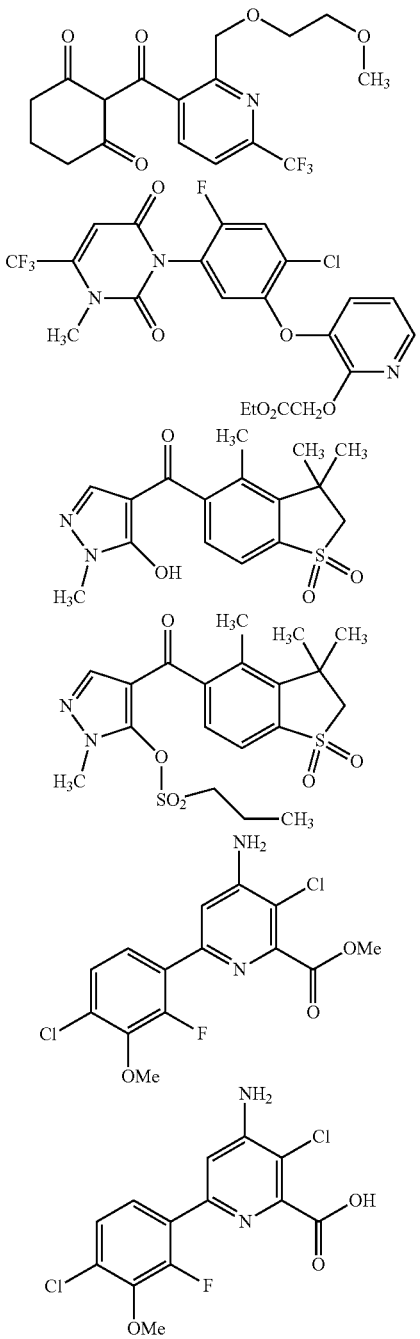

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more active substance, but it is preferably between 0.005 and 750 g/ha.

The examples which follow illustrate the invention.

A. CHEMICAL EXAMPLES

1. Synthesis of 2-(2-nitro-4-(methylsulfonyl)benzoyl)-2-(1-methyl-1,2,4-triazol-5-yl)acetonitrile, (Table example No. 1-1)

263 mg (1.0 mmol) of 2-nitro-4-(methylsulfonyl)benzoyl chloride are added at 0° C. to 122 mg (1.0 mmol) of 2-(1-methyl-1,2,4-triazol-5-yl)acetonitrile and 258 mg (2 mmol) of diisopropylethylamine. The mixture is then stirred at room temperature for 16 h. 1 ml of methanol is then added and, after 15 min, 2N HCl is added. The mixture is extracted with dichloromethane, dried over $Na_2SO_4$, evaporated and purified by means of RP-HPLC (acetonitrile/water). Yield 156 mg (45%).

Synthesis of 2-(1-methyl-1,2,4-triazol-5-yl)acetonitrile 10 g (88 mmol) of 2-hydroxymethyl-1-methyl-1,2,4-triazole are heated under RF with 40 ml of thionyl chloride for 30 min. The mixture is then concentrated by evaporation, taken up in 300 ml of acetonitrile and admixed with 42 g (173 mmol) of tetrabutylammonium cyanide. After 4 h, the mixture is diluted with ammonium chloride solution, ethyl acetate, and the organic phase is washed several times with sodium chloride solution. The residue after drying and concentration is purified by column chromatography (HepEE, EEMeOH). Yield 2.53 g (24%). $^1$H NMR, $CDCl_3$, 400 MHz: 7.88 (s, 1H), 3.99 (s, 6H).

2. Synthesis of 5-(2-methyl-3-(methylsulfonyl)-4-(trifluoromethyl)phenyl)-4-(1-methyl-1,2,4-triazol-5-yl)isoxazole, (Table example No. 3-9) and of 2-(2-methyl-3-(methylsulfonyl)-4-trifluoromethylbenzoyl)-2-(1-methyl-1,2,4-triazol-5-yl)acetonitrile, (Table example No. 1-9)

Synthesis of 1-(2-methyl-3-(methylsulfonyl)-4-trifluoromethylphenyl)-2-(1-methyl-1,2,4-triazol-5-yl)-1-oxoethane 683 mg (8.22 mmol) of 1-methyl-1,2,4-triazole in 20 ml of THF are admixed under argon at −78° C. with 3.3 ml (8.22 mmol) of butyllithium (2.5M, hexane). After 30 min, 1.22 g (8.63 mmol) of methyl iodide, dissolved in 2 ml of THF, are added, the cooling bath is removed and the mixture is left to reach RT. The mixture is cooled again to −78° C. and admixed with 3.3 ml (8.22 mmol) of butyllithium (2.5M, hexane). After 15 min, 1.22 g (4.12 mmol) of methyl 2-methyl-3-(methylsulfonyl)-4-trifluoromethylbenzoate are added and the mixture is left to thaw overnight. The mixture is quenched with ammonium chloride solution and extracted with EE. The organic phase is washed with $NaHCO_3$ solution and NaCl solution, dried, evaporated and purified by means of RP-HPLC (acetonitrile/water). Yield 255 mg (17%). $^1$H NMR, $CDCl_3$, 400 MHz: 7.90 (s, 1H), 7.82 (d, 1H), 7.72 (d, 1H), 5.57 (s, 1H), 3.85 (s, 3H), 3.27 (s, 3H), 2.84 (s, 3H).

Synthesis of 3-dimethylamino-1-(2-methyl-3-(methylsulfonyl)-4-(trifluoromethyl)phenyl)-2-(1-methyl-1,2,4-triazol-5-yl)prop-2-en-1-one 230 mg (0.64 mmol) of 1-(2-methyl-3-(methylsulfonyl)-4-(trifluoromethyl)phenyl)-2-(1-methyl-1,2,4-triazol-5-yl)-

1-oxoethane and 2.7 g of dimethylformamide dimethylacetal are stirred for 4 h at RT and then evaporated to dryness. The residue is used directly in the next step.

Synthesis of 5-(2-methyl-3-(methylsulfonyl)-4-(trifluoromethyl)phenyl)-4-(1-methyl-1,2,4-triazol-5-yl)isoxazole and 2-(2-methyl-3-(methylsulfonyl)-4-(trifluoromethyl)benzoyl)-2-(1-methyl-1,2,4-triazol-5-yl)acetonitrile 240 mg (0.57 mmol) of 3-dimethylamino-1-(2-methyl-3-(methylsulfonyl)-4-(trifluoromethyl)phenyl)-2-(1-methyl-1,2,4-triazol-5-yl)prop-2-en-1-one and 44 mg (0.63 mmol) of hydroxylammonium chloride in ethanol are heated for 16 h at RF. Then the mixture is concentrated by evaporation and the residue is taken up in ethyl acetate, washed with water and NaHCO₃ solution, and the organic phase is dried and concentrated in a rotary evaporator. Yield 137 mg (61%) of the isoxazole derivative (Table example No. 3-9).

The NaHCO₃ phase is acidified with 2N HCl and extracted with ethyl acetate. The organic phase is dried and concentrated in a rotary evaporator. Yield 38 mg (20%) of the acetonitrile derivative (Table example No. 1-9).

Treating the isoxazole derivative with 1.5 eq. of triethylamine in dichloromethane at RT for 30 min gives, following acidification with 2N HCl, the acetonitrile derivative in virtually quantitative yield.

3. Synthesis of 2-(2-methylsulfonyl)-4-trifluoromethylbenzoyl)-2-(1-methyl-tetrazol-5-yl)acetonitrile, (Table example No. 1-6)

189 mg (0.5 mmol) of 3-methylamino-3-methylsulfanyl-2-(2-(methylsulfonyl)-4-trifluoromethylbenzoyl)acrylonitrile and 33 mg (0.5 mmol) of sodium azide are heated at RF in a mixture of 2 ml of DMSO and 3 ml of acetonitrile for 2 h. The mixture is then poured onto ice-water and washed with ether, and the aqueous phase is acidified to pH 1-2. Extraction with dichloromethane, drying and concentration in a rotary evaporator are then carried out. Yield 138 mg (74%).

Synthesis of 3-methylamino-3-methylsulfanyl-2-(2-(methylsulfonyl)-4-trifluoromethylbenzoyl)acrylonitrile 1.03 g (3.54 mm) of 2-(2-(methylsulfonyl)-4-trifluoromethylbenzoyl)acetonitrile and 0.96 (7.07 mmol) of bismethylthio-N-methylformimine are heated to reflux for 16 h in 20 ml of toluene. After cooling, the resulting precipitate is filtered off with suction and washed with ether. Yield 0.93 g (70%). ¹H NMR, CDCl₃, 400 MHz: 11.90 (bs, 1H), 8.36 (s, 1H), 7.95 (d, 1H), 7.68 (d, 1H), 3.32 (d, 2H), 3.28 (s, 3H), 2.79 (s, 3H).

Synthesis of 2-(2-(methylsulfonyl)-4-trifluoromethylbenzoyl)acetonitrile 1.10 g of magnesium chloride (11.5 mmol) in 15 ml of acetonitrile are admixed at 0° C. with 2.0 g (11.4 mmol) of benzyl cyanoacetate and 2.3 g (22.9 mmol) of triethylamine. After stirring for 20 min at 0° C., 3.27 g (11.4 mmol) of 2-(methylsulfonyl)-4-trifluoromethylbenzoyl chloride are added in portions. The mixture is stirred for 16 h at RT, acidified with 2n HCl and extracted with ether. The organic phase is dried and concentrated in a rotary evaporator. Yield 2.74 g (56%; ¹H-NMR, CDCl₃, 400 MHz: 14.20 (bs, 1H), 8.43 (s, 1H), 8.05 (d, 1H), 7.82 (d, 1H), 5.40 (s, 2H), 3.30 (s, 3H)) of benzyl 2-(2-(methylsulfonyl)-4-trifluoromethylbenzoyl)cyanoacetate, which, after adding 0.65 g (1 eq) of triethylamine in THF, is hydrogenated for 2 h. After filtration, the mixture is diluted with ethyl acetate and washed with 2N HCl, NaHCO₃ solution and sodium chloride solution. Yield 1.41 g (75%). ¹H NMR, CDCl₃, 400 MHz: 8.36 (s, 1H), 8.04 (d, 1H), 7.63 (d, 1H), 4.03 (s, 2H), 3.21 (s, 3H).

The examples listed in the tables below were prepared analogously to the abovementioned methods or are obtainable analogously to the abovementioned methods. The compounds listed in the tables below are very particularly preferred.

The abbreviations used mean:

| Et = ethyl | Me = methyl | Pr = n-propyl | i-Pr = isopropyl |
|---|---|---|---|
| c-Pr = cyclopropyl | Ph = phenyl | Ac = acetyl | Bz = benzoyl |

TABLE 1

Compounds according to the invention of the general formula (I), in which A is CY, W is hydrogen and Q is Q¹

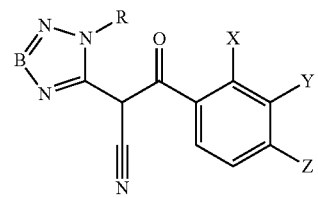

| No. | B | R | X | Y | Z | Physical data (¹H-NMR, CDCl₃, 400 MHz) |
|---|---|---|---|---|---|---|
| 1-1 | CH | Me= | NO₂ | H | SO₂Me | 8.70 (d, 1H), 8.28 (dd, 1H), 8.02 (s, 1H), 7.80 (d, 1H), 4.17 (s, 3H), 3.16 (s, 3H) |
| 1-2 | N | Me | NO₂ | H | SO₂Me | |
| 1-3 | CH | Me | Cl | H | SO₂Me | 8.05 (d, 1H), 8.02 (s, 1H), 7.91 (dd, 1H), 7.62 (d, 1H), 4.18 (s, 3H), 3.10 (s, 3H) |
| 1-4 | N | Me | Cl | H | SO₂Me | |
| 1-5 | CH | Me | SO₂Me | H | CF₃ | 8.56 (s, 1H), 8.24 (s, 1H), 8.23 (d, 1H), 7.88 (d, 1H), 4.18 (s, 3H), 3.45 (s, 3H) |
| 1-6 | N | Me | SO₂Me | H | CF₃ | 8.22 (s, 1H), 8.17 (d, 1H), 7.88 (d, 1H), 4.01 (s, 3H), 3.43 (s, 3H) |
| 1-7 | CH | Me | Me | SMe | CF₃ | |
| 1-8 | N | Me | Me | SMe | CF₃ | |

TABLE 1-continued

Compounds according to the invention of the general formula (I), in which A is CY, W is hydrogen and Q is Q¹

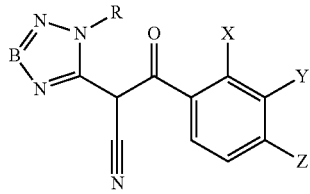

| No. | B | R | X | Y | Z | Physical data ($^1$H-NMR, CDCl$_3$, 400 MHz) |
|---|---|---|---|---|---|---|
| 1-9 | CH | Me | Me | SO$_2$Me | CF$_3$ | 8.02 (s, 1H), 7.88 (d, 1H), 7.68 (d, 1H), 4.18 (s, 3H), 3.24 (s, 3H), 2.78 (s, 3H) |
| 1-10 | N | Me | Me | SO$_2$Me | CF$_3$ | |
| 1-11 | CH | Me | Me | 4,5-dihydro-1,2-oxazol-3-yl | SO$_2$Me | 8.17 (d, 1H), 8.00 (s, 1H), 7.64 (d, 1H), 4.59 (t, 2H), 4.18 (s, 3H), 3.38 (brs, 2H), 3.20 (s, 3H), 2.37 (s, 3H) |
| 1-12 | N | Me | Me | 4,5-dihydro-1,2-oxazol-3-yl | SO$_2$Me | |
| 1-13 | CH | Me | Me | pyrazol-1-yl | SO$_2$Me | |
| 1-14 | N | Me | Me | pyrazol-1-yl | SO$_2$Me | |
| 1-15 | CH | Me | Me | SO$_2$Me | SO$_2$Me | 8.36 (d, 1H), 8.02 (s, 1H), 7.71 (d, 1H), 4.18 (s, 3H), 3.57 (s, 3H), 3.45 (s, 3H), 2.78 (s, 3H) |
| 1-16 | N | Me | Me | SO$_2$Me | SO$_2$Me | |
| 1-17 | CH | Me | Et | SMe | CF$_3$ | |
| 1-18 | N | Me | Et | SMe | CF$_3$ | |
| 1-19 | CH | Me | Et | SO$_2$Me | CF$_3$ | |
| 1-20 | N | Me | Et | SO$_2$Me | CF$_3$ | |
| 1-21 | CH | Me | Et | SMe | Cl | |
| 1-22 | N | Me | Et | SMe | Cl | |
| 1-23 | CH | Me | Et | SMe | Br | |
| 1-24 | N | Me | Et | SMe | Br | |
| 1-25 | CH | Me | Pr | SMe | CF$_3$ | |
| 1-26 | N | Me | Pr | SMe | CF$_3$ | |
| 1-27 | CH | Me | Cpr | SMe | CF$_3$ | |
| 1-28 | N | Me | Cpr | SMe | CF$_3$ | |
| 1-29 | CH | Me | OMe | SMe | CF$_3$ | |
| 1-30 | N | Me | OMe | SMe | CF$_3$ | |
| 1-31 | CH | Me | OMe | SO$_2$Me | CF$_3$ | |
| 1-32 | N | Me | OMe | SO$_2$Me | CF$_3$ | |
| 1-33 | CH | Me | Cl | SO$_2$Me | Me | |
| 1-34 | N | Me | Cl | SO$_2$Me | Me | |
| 1-35 | CH | Me | Cl | SO$_2$Et | Me | |
| 1-36 | N | Me | Cl | SO$_2$Et | Me | |
| 1-37 | CH | Me | Cl | SO$_2$Me | CF$_3$ | |
| 1-38 | N | Me | Cl | SO$_2$Me | CF$_3$ | |
| 1-39 | CH | Me | Cl | OC$_2$H$_4$OMe | Cl | |
| 1-40 | N | Me | Cl | OC$_2$H$_4$OMe | Cl | |
| 1-41 | CH | Me | Cl | SMe | Cl | |
| 1-42 | N | Me | Cl | SMe | Cl | |
| 1-43 | CH | Me | Cl | SO$_2$Me | Cl | |
| 1-44 | N | Me | Cl | SO$_2$Me | Cl | |
| 1-45 | CH | Me | Cl | CH$_2$OMe | SO$_2$Me | |
| 1-46 | N | Me | Cl | CH$_2$OMe | SO$_2$Me | |
| 1-47 | CH | Me | Cl | CH$_2$OC$_2$H$_4$OMe | SO$_2$Me | |
| 1-48 | N | Me | Cl | CH$_2$OC$_2$H$_4$OMe | SO$_2$Me | |
| 1-49 | CH | Me | Cl | CH$_2$OCH$_2$CF$_3$ | SO$_2$Me | 8.16 (d, 1H), 8.01 (s, 1H), 7.60 (d, 1H), 5.39 (s, 2H), 4.18 (s, 3H), 4.04 (q, 2H), 3.20 (s, 3H) |
| 1-50 | N | Me | Cl | CH$_2$OCH$_2$CF$_3$ | SO$_2$Me | 8.23 (d, 1H), 7.70 (d, 1H), 5.40 (s, 2H), 4.37 (s, 3H), 4.06 (q, 2H), 3.26 (s, 3H) |
| 1-51 | CH | Me | Cl | CH$_2$OCH$_2$—tetrahydrofuran-2-yl | SO$_2$Me | 8.15 (d, 1H), 8.01 (s, 1H), 7.56 (d, 1H), 5.22 (s, 2H), 4.18 (s, 3H), 4.11 (m, 1H), 3.84 (m, 1H), 3.78 (m, 1H), 3.70-3.60 (m, 2H), 3.30 (s, 3H), 2.01-1.80 (m, 3H), 1.68-1.58 (m, 1H) |
| 1-52 | N | Me | Cl | CH$_2$OCH$_2$—tetrahydrofuran-2-yl | SO$_2$Me | |

TABLE 1-continued

Compounds according to the invention of the general formula (I), in which A is CY, W is hydrogen and Q is $Q^1$

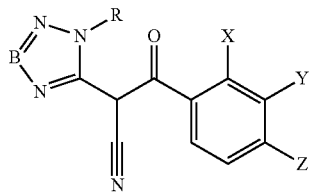

| No. | B | R | X | Y | Z | Physical data ($^1$H-NMR, CDCl$_3$, 400 MHz) |
|---|---|---|---|---|---|---|
| 1-53 | CH | Me | Cl | 4,5-dihydro-1,2-oxazol-3-yl | SO$_2$Me | |
| 1-54 | N | Me | Cl | 4,5-dihydro-1,2-oxazol-3-yl | SO$_2$Me | |
| 1-55 | CH | Me | Cl | 5-methoxymethyl-4,5-dihydro-1,2-oxazol-3 yl | SO$_2$Me | |
| 1-56 | N | Me | Cl | 5-methoxymethyl-4,5-dihydro-1,2-oxazol-3 yl | SO$_2$Me | |
| 1-57 | CH | Me | Cl | 5-cyanomethyl-4,5-dihydro-1,2-oxazol-3-yl | SO$_2$Et | 8.10 (d, 1H), 8.04 (s, 1H), 7.70 (d, 1H), 5.67 (m, 1H), 4.18 (s, 3H), 3.77 (dd, 1H), 3.38 (q, 2H), 3.27 (m, 2H), 2.95 (m, 1H), 2.84 (dd, 1H), 1.28 (t, 3H) |
| 1-58 | N | Me | Cl | 5-cyanomethyl-4,5-dihydro-1,2-oxazol-3-yl | SO$_2$Et | |
| 1-59 | CH | Me | Cl | OMe | SO$_2$Me | |
| 1-60 | N | Me | Cl | OMe | SO$_2$Me | |
| 1-61 | CH | Me | Cl | OEt | SO$_2$Me | |
| 1-62 | N | Me | Cl | OEt | SO$_2$Me | |
| 1-63 | CH | Me | Cl | OPr | SO$_2$Me | |
| 1-64 | N | Me | Cl | OPr | SO$_2$Me | |
| 1-65 | CH | Me | Cl | OCH$_2$c—Pr | SO$_2$Me | |
| 1-66 | N | Me | Cl | OCH$_2$c—Pr | SO$_2$Me | |
| 1-67 | CH | Me | Cl | OC$_2$H$_4$OMe | SO$_2$Me | |
| 1-68 | N | Me | Cl | OC$_2$H$_4$OMe | SO$_2$Me | |
| 1-69 | CH | Me | Cl | SMe | SO$_2$Me | |
| 1-70 | N | Me | Cl | SMe | SO$_2$Me | |

TABLE 2

Compounds according to the invention of the general formula (I), in which A is N, W is hydrogen and Q is $Q^1$

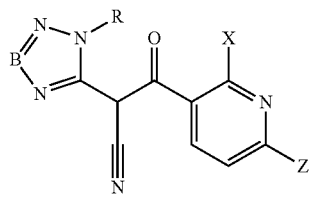

| No. | B | R | X | Z | Physical data ($^1$H-NMR, DMSO-d$_6$, 400 MHz) |
|---|---|---|---|---|---|
| 2-1 | CH | Me | Me | CF$_3$ | |
| 2-2 | N | Me | Me | CF$_3$ | |
| 2-3 | CH | Me | CH$_2$OMe | CF$_3$ | |
| 2-4 | N | Me | CH$_2$OMe | CF$_3$ | |
| 2-5 | CH | Me | CH$_2$OC$_2$H$_4$OMe | CF$_3$ | |
| 2-6 | N | Me | CH$_2$OC$_2$H$_4$OMe | CF$_3$ | |
| 2-7 | CH | Me | CH$_2$OCH$_2$cPr | CF$_3$ | |
| 2-8 | N | Me | CH$_2$OCH$_2$cPr | CF$_3$ | |
| 2-9 | CH | Me | Cl | CF$_3$ | |
| 2-10 | N | Me | Cl | CF$_3$ | |
| 2-11 | CH | Me | Br | CF$_3$ | |
| 2-12 | N | Me | Br | CF$_3$ | |

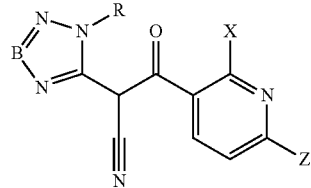

TABLE 3

Compounds according to the invention of the general formula (I), in which A is CY, W is hydrogen and Q is $Q^1$

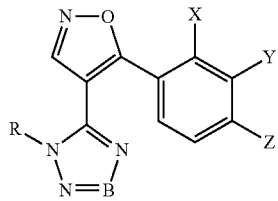

| No. | B | R | X | Y | Z | Physical data ($^1$H-NMR, CDCl$_3$, 400 MHz) |
|---|---|---|---|---|---|---|
| 3-1 | CH | Me | NO$_2$ | H | SO$_2$Me | |
| 3-2 | N | Me | NO$_2$ | H | SO$_2$Me | |
| 3-3 | CH | Me | Cl | H | SO$_2$Me | |
| 3-4 | N | Me | Cl | H | SO$_2$Me | |
| 3-5 | CH | Me | SO$_2$Me | H | CF$_3$ | |
| 3-6 | N | Me | SO$_2$Me | H | CF$_3$ | |
| 3-7 | CH | Me | Me | SMe | CF$_3$ | |
| 3-8 | N | Me | Me | SMe | CF$_3$ | |
| 3-9 | CH | Me | Me | SO$_2$Me | CF$_3$ | 8.67 (s, 1H), 7.86 (d, 1H), 7.87 (s, 1H), 7.78 (d, 1H), 3.82 (s, 3H), 3.26 (s, 3H), 2.61 (s, 3H) |
| 3-10 | N | Me | Me | SO$_2$Me | CF$_3$ | |
| 3-11 | CH | Me | Me | 4,5-dihydro-1,2-oxazol-3-yl | SO$_2$Me | |
| 3-12 | N | Me | Me | 4,5-dihydro-1,2-oxazol-3-yl | SO$_2$Me | |
| 3-13 | CH | Me | Me | pyrazol-1-yl | SO$_2$Me | |
| 3-14 | N | Me | Me | pyrazol-1-yl | SO$_2$Me | |
| 3-15 | CH | Me | Me | SO$_2$Me | SO$_2$Me | |
| 3-16 | N | Me | Me | SO$_2$Me | SO$_2$Me | |
| 3-17 | CH | Me | Et | SMe | CF$_3$ | |
| 3-18 | N | Me | Et | SMe | CF$_3$ | |
| 3-19 | CH | Me | Et | SO$_2$Me | CF$_3$ | |
| 3-20 | N | Me | Et | SO$_2$Me | CF$_3$ | |
| 3-21 | CH | Me | Et | SMe | Cl | |
| 3-22 | N | Me | Et | SMe | Cl | |
| 3-23 | CH | Me | Et | SMe | Br | |
| 3-24 | N | Me | Et | SMe | Br | |
| 3-25 | CH | Me | Pr | SMe | CF$_3$ | |
| 3-26 | N | Me | Pr | SMe | CF$_3$ | |
| 3-27 | CH | Me | Cpr | SMe | CF$_3$ | |
| 3-28 | N | Me | Cpr | SMe | CF$_3$ | |
| 3-29 | CH | Me | OMe | SMe | CF$_3$ | |
| 3-30 | N | Me | OMe | SMe | CF$_3$ | |
| 3-31 | CH | Me | OMe | SO$_2$Me | CF$_3$ | |
| 3-32 | N | Me | OMe | SO$_2$Me | CF$_3$ | |
| 3-33 | CH | Me | Cl | SO$_2$Me | Me | |
| 3-34 | N | Me | Cl | SO$_2$Me | Me | |
| 3-35 | CH | Me | Cl | SO$_2$Et | Me | |
| 3-36 | N | Me | Cl | SO$_2$Et | Me | |
| 3-37 | CH | Me | Cl | SO$_2$Me | CF$_3$ | |
| 3-38 | N | Me | Cl | SO$_2$Me | CF$_3$ | |
| 3-39 | CH | Me | Cl | OC$_2$H$_4$OMe | Cl | |
| 3-40 | N | Me | Cl | OC$_2$H$_4$OMe | Cl | |
| 3-41 | CH | Me | Cl | SMe | Cl | |
| 3-42 | N | Me | Cl | SMe | Cl | |
| 3-43 | CH | Me | Cl | SO$_2$Me | Cl | |
| 3-44 | N | Me | Cl | SO$_2$Me | Cl | |
| 3-45 | CH | Me | Cl | CH$_2$OMe | SO$_2$Me | |
| 3-46 | N | Me | Cl | CH$_2$OMe | SO$_2$Me | |
| 3-47 | CH | Me | Cl | CH$_2$OC$_2$H$_4$OMe | SO$_2$Me | |
| 3-48 | N | Me | Cl | CH$_2$OC$_2$H$_4$OMe | SO$_2$Me | |
| 3-49 | CH | Me | Cl | CH$_2$OCH$_2$CF$_3$ | SO$_2$Me | |
| 3-50 | N | Me | Cl | CH$_2$OCH$_2$CF$_3$ | SO$_2$Me | |
| 3-51 | CH | Me | Cl | CH$_2$OCH$_2$—tetrahydrofuran-2-yl | SO$_2$Me | |
| 3-52 | N | Me | Cl | CH$_2$OCH$_2$—tetrahydrofuran-2-yl | SO$_2$Me | |
| 3-53 | CH | Me | Cl | 4,5-dihydro-1,2-oxazol-3-yl | SO$_2$Me | |
| 3-54 | N | Me | Cl | 4,5-dihydro-1,2-oxazol-3-yl | SO$_2$Me | |

TABLE 3-continued

Compounds according to the invention of the general formula (I),
in which A is CY, W is hydrogen and Q is $Q^1$

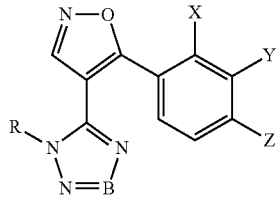

| No. | B | R | X | Y | Z | Physical data ($^1$H-NMR, CDCl$_3$, 400 MHz) |
|---|---|---|---|---|---|---|
| 3-55 | CH | Me | Cl | 5-methoxymethyl-4,5-dihydro-1,2-oxazol-3-yl | SO$_2$Me | |
| 3-56 | N | Me | Cl | 5-methoxymethyl-4,5-dihydro-1,2-oxazol-3-yl | SO$_2$Me | |
| 3-57 | CH | Me | Cl | 5-cyanomethyl-4,5-dihydro-1,2-oxazol-3-yl | SO$_2$Et | |
| 3-58 | N | Me | Cl | 5-cyanomethyl-4,5-dihydro-1,2-oxazol-3-yl | SO$_2$Et | |
| 3-59 | CH | Me | Cl | OMe | SO$_2$Me | |
| 3-60 | N | Me | Cl | OMe | SO$_2$Me | |
| 3-61 | CH | Me | Cl | OEt | SO$_2$Me | |
| 3-62 | N | Me | Cl | OEt | SO$_2$Me | |
| 3-63 | CH | Me | Cl | OPr | SO$_2$Me | |
| 3-64 | N | Me | Cl | OPr | SO$_2$Me | |
| 3-65 | CH | Me | Cl | OCH$_2$c—Pr | SO$_2$Me | |
| 3-66 | N | Me | Cl | OCH$_2$c—Pr | SO$_2$Me | |
| 3-67 | CH | Me | Cl | OC$_2$H$_4$OMe | SO$_2$Me | |
| 3-68 | N | Me | Cl | OC$_2$H$_4$OMe | SO$_2$Me | |
| 3-69 | CH | Me | Cl | SMe | SO$_2$Me | |
| 3-70 | N | Me | Cl | SMe | SO$_2$Me | |

TABLE 4

Compounds according to the invention of the general formula (I),
in which A is N, W is hydrogen and Q is $Q^1$

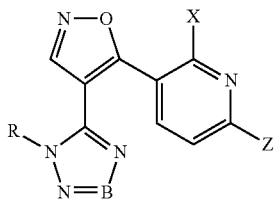

| No. | B | R | X | Z | Physical data ($^1$H-NMR, DMSO-d$_6$, 400 MHz) |
|---|---|---|---|---|---|
| 4-1 | CH | Me | Me | CF$_3$ | |
| 4-2 | N | Me | Me | CF$_3$ | |
| 4-3 | CH | Me | CH$_2$OMe | CF$_3$ | |
| 4-4 | N | Me | CH$_2$OMe | CF$_3$ | |
| 4-5 | CH | Me | CH$_2$OC$_2$H$_4$OMe | CF$_3$ | |
| 4-6 | N | Me | CH$_2$OC$_2$H$_4$OMe | CF$_3$ | |
| 4-7 | CH | Me | CH$_2$OCH$_2$cPr | CF$_3$ | |
| 4-8 | N | Me | CH$_2$OCH$_2$cPr | CF$_3$ | |
| 4-9 | CH | Me | Cl | CF$_3$ | |
| 4-10 | N | Me | Cl | CF$_3$ | |
| 4-11 | CH | Me | Br | CF$_3$ | |
| 4-12 | N | Me | Br | CF$_3$ | |

B. FORMULATION EXAMPLES a) A dusting product is obtained by mixing 10 parts by weight of a compound of the formula (I) and/or salts thereof and 90 parts by weight of talc as an inert substance, and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
   75 parts by weight of a compound of the formula (I) and/or salts thereof,
   10 parts by weight of calcium lignosulfonate,
   5 parts by weight of sodium lauryl sulfate,
   3 parts by weight of polyvinyl alcohol and
   7 parts by weight of kaolin, grinding the mixture in a pinned-disk mill and granulating the powder in a fluidized bed by spraying on water as a granulating liquid.

f) Water-dispersible granules are also obtained by homogenizing and precomminuting 25 parts by weight of a compound of the formula (I) and/or salts thereof,
5 parts by weight of sodium 2,2'-dinaphthylmethane-6,6'-disulfonate
2 parts by weight of sodium oleoylmethyltaurate,
1 part by weight of polyvinyl alcohol,
17 parts by weight of calcium carbonate and
50 parts by weight of water
in a colloid mill, then grinding the mixture in a bead mill and atomizing and drying the resulting suspension in a spray tower by means of a one-phase nozzle.

C. BIOLOGICAL EXAMPLES

1. Pre-Emergence Herbicidal Action Against Weed Plants

Seeds of monocotyledonous and dicotyledonous weed plants and crop plants are placed in wood-fiber pots in sandy loam and covered with soil. The compounds according to the invention formulated in the form of wettable powders (WP) or as emulsion concentrates (EC) are then applied to the surface of the covering soil as an aqueous suspension or emulsion at a water application rate of 600 to 800 I/ha (converted) with addition of 0.2% wetting agent. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). The compounds Nos. 1-1, 1-3, 1-9, 1-11, 1-15, 1-49 and 3-9, at an application rate of 320 g/ha, each show at least 80% efficacy against *Stellaria media* and *Amaranthus retroflexus*. The compounds Nos. 1-9, 1-11 and 1-15, at an application rate of 320 g/ha, each show at least 80% efficacy against *Cyperus serotinus* and *Setaria viridis*. The compounds Nos. 1-9, 1-11, 1-15, 1-49 and 3-9, at an application rate of 320 g/ha, each show an at least 80% efficacy against *Echinochloa crus galli* and *Veronica persica*.

2. Post-Emergence Herbicidal Action Against Weed Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention formulated in the form of wettable powders (WP) or as emulsion concentrates (EC) are then sprayed onto the green parts of the plants as an aqueous suspension or emulsion at a water application rate of 600 to 800 I/ha (converted) with addition of 0.2% wetting agent. After the test plants have been left to stand in the greenhouse under optimal growth conditions for about 3 weeks, the action of the formulations is assessed visually in comparison to untreated controls (herbicidal action in percent (%): 100% activity=the plants have died, 0% activity=like control plants). For example, compounds Nos. 1-3, 1-9, 1-11, 1-15, 1-49 and 3-9, at an application rate of 80 g/ha, each show an at least 80% efficacy against *Abutilon theophrasti* and *Veronica persica*. The compounds Nos. 1-3, 1-9, 1-11, 1-15, 1-49, and 3-9, at an application rate of 80 g/ha, each show an at least 80% efficacy against *Amaranthus retroflexus* and *Stellaria media*.

The invention claimed is:
1. A tetrazol-5-yl- and/or triazol-5-yl-aryl compound of formula (I) and/or a salt thereof

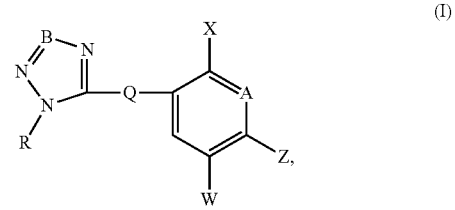

in which
Q is $Q^1$ or $Q^2$

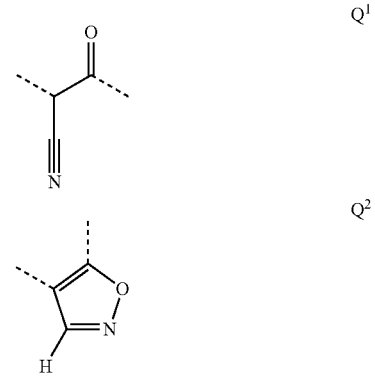

where in each case the oxygen-carrying carbon atom is bonded to the aryl moiety of the compound of the formula (I),
A is N or CY,
B is N or CH,
X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-S(O)$_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkylheteroaryl, $(C_1-C_6)$-alkylheterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C$ (O)N(R$^1$)$_2$, OC(O)N(R$^1$)$_2$, CO(NOR$^1$)R$^1$, NR$^1$SO$_2$R$^2$, NR$^1$COR$^1$, OR$^1$, OSO$_2$R$^2$, S(O)$_n$R$^2$, SO$_2$OR$^1$, SO$_2$N(R$^1$)$_2$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-OSO$_2$R$^2$, (C$_1$-C$_6$)-alkyl-CO$_2$R$^1$, (C$_1$-C$_6$)-alkyl-CN, (C$_1$-C$_6$)-alkyl-SO$_2$OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, N(R$^1$)$_2$, P(O)(OR$^5$)$_2$, CH$_2$P(O)(OR$^5$)$_2$, (C$_1$-C$_6$)-alkylphenyl, (C$_1$-C$_6$)-alkylheteroaryl, (C$_1$-C$_6$)-alkylheterocyclyl, phenyl, heteroaryl or heterocyclyl where the 6 last-mentioned radicals are each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy, (C$_1$-C$_6$)-alkoxy-(C$_1$-C$_4$)-alkyl and cyanomethyl, and where heterocyclyl carries n oxo groups, Z is halogen, cyano, thiocyanato, nitro, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, (C$_3$-C$_6$)-cycloalkyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, COR$^1$, COOR$^1$, OCOOR$^1$, NR$^1$COOR$^1$, C(O)N(R$^1$)$_2$, NR$^1$C(O)N(R$^1$)$_2$, OC(O)N(R$^1$)$_2$, C(O)NR$^1$OR$^1$, OSO$_2$R$^2$, S(O)$_n$R$^2$, SO$_2$OR$^1$, SO$_2$N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-OSO$_2$R$^2$, (C$_1$-C$_6$)-alkyl-CO$_2$R$^1$, (C$_1$-C$_6$)-alkyl-SO$_2$OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, N(R$^1$)$_2$, P(O)(OR$^5$)$_2$, heteroaryl, heterocyclyl or phenyl, where the three last-mentioned radicals are each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy and halo-(C$_1$-C$_6$)-alkoxy, and where heterocyclyl carries n oxo groups, Z may also be hydrogen, (C$_1$-C$_6$)-alkyl or (C$_1$-C$_6$)-alkoxy if Y is the S(O)$_n$R$^2$ radical, W is hydrogen, R is hydrogen, (C$_1$-C$_8$)-alkyl, halo-(C$_1$-C$_6$)-alkyl, (C$_2$-C$_8$)-alkenyl, halo-(C$_2$-C$_8$)-alkenyl, (C$_2$-C$_8$)-alkynyl, halo-(C$_2$-C$_8$)-alkynyl or (C$_3$-C$_7$)-cycloalkylmethyl, where these seven aforementioned radicals are each substituted by s radicals from the group consisting of hydroxy, nitro, cyano, SiR$^5$$_3$, PO(OR$^5$)$_2$, S(O)$_n$—(C$_1$-C$_6$)-alkyl, S(O)$_n$—(C$_1$-C$_6$)-haloalkyl, (C$_1$-C$_6$)-alkoxy, halo-(C$_1$-C$_6$)-alkoxy, N(R$^3$)$_2$, COR$^3$, COOR$^3$, OCOR$^3$, NR$^3$COR$^3$, NR$^3$SO$_2$R$^4$, O(C$_1$-C$_2$)-alkyl-(C$_3$-C$_6$)-cycloalkyl, (C$_3$-C$_6$)-cycloalkyl, heteroaryl, heterocyclyl and phenyl, where the three last-mentioned radicals are each substituted by s radicals from the group consisting of methyl, ethyl, methoxy, trifluoromethyl, cyano and halogen, and where heterocyclyl carries n oxo groups, or R is (C$_3$-C$_7$)-cycloalkyl, heteroaryl, heterocyclyl or phenyl, where these four aforementioned radicals are each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy and (C$_1$-C$_6$)-alkoxy-(C$_1$-C$_4$)-alkyl, and where heterocyclyl carries n oxo groups, R$^1$ is hydrogen, (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_6$)-cycloalkyl, (C$_3$-C$_6$)-cycloalkenyl, (C$_3$-C$_6$)-halocycloalkyl, (C$_1$-C$_6$)-alkyl-O—(C$_1$-C$_6$)-alkyl, (C$_3$-C$_6$)-cycloalkyl-(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-hetero aryl, (C$_1$-C$_6$)-alkyl-O-heterocyclyl, (C$_1$-C$_6$)-alkyl-NR$^3$-heteroaryl or (C$_1$-C$_6$)-alkyl-NR$^3$-heterocyclyl, where the 21 last-mentioned radicals are each substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl carries n oxo groups, R$^2$ is (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_6$)-cycloalkyl, (C$_3$-C$_6$)-cycloalkenyl, (C$_3$-C$_6$)-halocycloalkyl, (C$_1$-C$_6$)-alkyl-O—(C$_1$-C$_6$)-alkyl, (C$_3$-C$_6$)-cycloalkyl-(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl or (C$_1$-C$_6$)-alkyl-NR$^3$-heterocyclyl, where the 21 last-mentioned radicals are each substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl carries n oxo groups, R$^3$ is hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl, R$^4$ is (C$_1$-C$_6$)-alkyl, (C$_2$-C$_6$)-alkenyl or (C$_2$-C$_6$)-alkynyl, R$^5$ is methyl or ethyl, n is 0, 1 or 2, s is 0, 1, 2 or 3.

2. The compound as claimed in claim 1, in which

Q is Q$^1$ or Q$^2$,

A is N or CY,

B is N or CH,

X is nitro, halogen, cyano, thiocyanato, (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, (C$_3$-C$_6$)-cycloalkyl, halo-(C$_3$-C$_6$)-cycloalkyl, (C$_1$-C$_6$)-alkyl-O—(C$_1$-C$_6$)-alkyl, (C$_3$-C$_6$)-cycloalkyl-(C$_1$-C$_6$)-alkyl, halo-(C$_3$-C$_6$)-cycloalkyl-(C$_1$-C$_6$)-alkyl, COR$^1$, OR$^1$, OCOR$^1$, OSO$_2$R$^2$, S(O)$_n$R$^2$, SO$_2$OR$^1$, SO$_2$N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-OSO$_2$R$^2$, (C$_1$-C$_6$)-alkyl-CO$_2$R$^1$, (C$_1$-C$_6$)-alkyl-SO$_2$OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$ or (C$_1$-C$_6$)-alkyl-NR$^1$SO$_2$R$^2$, (C$_1$-C$_6$)-alkylheteroaryl, (C$_1$-C$_6$)-alkylheterocyclyl, where the two last-mentioned radicals are each substituted by s radicals from the group consisting of halogen, (C$_1$-C$_6$)-alkyl, halo-(C$_1$-C$_6$)-alkyl, S(O)$_n$—(C$_1$-C$_6$)-alkyl, (C$_1$-C$_6$)-alkoxy and halo-(C$_1$-C$_6$)-alkoxy, and where heterocyclyl carries n oxo groups, Y is hydrogen, nitro, halogen, cyano, thiocyanato, (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, (C$_3$-C$_6$)-cycloalkyl, (C$_3$-C$_6$)-cycloalkenyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, COR$^1$, OR$^1$, COOR$^1$, OSO$_2$R$^2$, S(O)$_n$R$^2$, SO$_2$OR$^1$, SO$_2$N(R$^1$)$_2$, N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-OSO$_2$R$^2$, (C$_1$-C$_6$)-alkyl-CO$_2$R$^1$, (C$_1$-

$C_6$)-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z is halogen, cyano, thiocyanato, nitro, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $C(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$ or 1,2,4-triazol-1-yl, or may also be hydrogen, $(C_1-C_6)$-alkyl or $(C_1-C_6)$-alkoxy if Y is the $S(O)_nR^2$ radical, W is hydrogen, R is $(C_1-C_8)$-alkyl, halo-$(C_1-C_6)$-alkyl, $(C_2-C_8)$-alkenyl, halo-$(C_2-C_6)$-alkenyl, $(C_2-C_8)$-alkynyl, halo-$(C_2-C_6)$-alkynyl or $(C_3-C_7)$-cycloalkylmethyl, where these seven aforementioned radicals are each substituted by s radicals from the group consisting of the group cyano, $S(O)_n$—$(C_1-C_6)$-alkyl, $S(O)_n$—$(C_1-C_6)$-haloalkyl, $(C_1-C_6)$-alkoxy and halo-$(C_1-C_6)$-alkoxy, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries n oxo groups, $R^2$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_6-C6)$-alkyl-O-heterocyclyl, $(C_1-C_6)$-alkyl-$NR^3$-heteroaryl or $(C_1-C_6)$-alkyl-$NR^3$-heterocyclyl, where these 15 last-mentioned radicals are each substituted by s radicals from the group consisting of cyano, halogen, nitro, $OR^3$, $S(O)_nR^4$, $N(R^3)_2$, $NR^3OR^3$, $NR^3SO_2R^4$, $COR^3$, $OCOR^3$, $NR^3COR^3$, $CO_2R^3$, $CON(R^3)_2$ and $(C_1-C_4)$-alkoxy-$(C_2-C_6)$-alkoxycarbonyl, and where heterocyclyl carries n oxo groups, $R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ is $(C_1-C_6)$-alkyl, $(C_2-C_6)$-alkenyl or $(C_2-C_6)$-alkynyl, n is 0, 1 or 2, s is 0, 1, 2 or 3.

3. The compound as claimed in claim 1, in which

Q is $Q^1$ or $Q^2$,

A is N or CY,

B is N or CH,

X is nitro, halogen, cyano, $(C_1-C_6)$-alkyl, halo-$(C_1-C_6)$-alkyl, $(C_3-C_6)$-cycloalkyl, $OR^1$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-hetero aryl or $(C_1-C_6)$-alkylheterocyclyl, where the two last-mentioned radicals are substituted in each case by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Y is hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 last-mentioned radicals are each substituted by s radicals from the group halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z is halogen, cyano, nitro, halo-$(C_1-C_6)$-alkyl, $(C_3-C_6)$-cycloalkyl, $S(O)_nR^2$ or 1,2,4-triazol-1-yl, or else Z may be hydrogen, methyl, methoxy or ethoxy if Y is the radical $S(O)_nR^2$, W is hydrogen, R is $(C_1-C_8)$-alkyl, halo-$(C_1-C_6)$-alkyl, $(C_2-C_8)$-alkenyl, halo-$(C—C_6)$-alkenyl, $(C_2-C_8)$-alkynyl, halo-$(C_2-C_6)$-alkynyl or $(C_3-C_7)$-cycloalkylmethyl, where these seven radicals are each substituted by s radicals from the group consisting of cyano, $S(O)_n$—$(C_1-C_6)$-alkyl, $S(O)_n$—$(C_1-C_6)$-haloalkyl, $(C_1-C_6)$-alkoxy and halo-$(C_1-C_6)$-alkoxy, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries n oxo groups, $R^2$ is $(C_1-C_6)$-alkyl, $(C_3-C_6)$-cycloalkyl or $(C_3-C_6)$-cycloalkyl-$(C_1-C_6)$-alkyl, where these three aforementioned radicals are each substituted by s radicals from the group consisting of halogen and $OR^3$, $R^3$ is hydrogen or $(C_1-C_6)$-alkyl, $R^4$ is $(C_1-C_6)$-alkyl, n is 0, 1 or 2, s is 0, 1, 2 or 3.

4. A herbicidal composition comprising a herbicidally effective content of at least one compound as claimed in claim 1.

5. The herbicidal composition as claimed in claim 4 in a mixture with one or more formulation auxiliaries.

6. The herbicidal composition as claimed in claim 4, comprising at least one further pesticidally active substance selected from the group consisting of insecticides, acaricides, herbicides, fungicides, safeners and growth regulators.

7. The herbicidal composition as claimed in claim 6, comprising a safener.

8. The herbicidal composition as claimed in claim 7, comprising cyprosulfamide, cloquintocet-mexyl, mefenpyr-diethyl or isoxadifen-ethyl.

9. The herbicidal composition as claimed in claim 6, comprising a further herbicide.

10. A method for controlling unwanted plants, comprising applying an effective amount of at least one compound as claimed in claim 1 to the unwanted plants and/or to a site of unwanted vegetation.

11. A compound as claimed in claim 1 capable of being used for controlling one or more unwanted plants.

12. The compound as claimed in claim 11, capable of being used for controlling one or more unwanted plants in a crop of a useful plant.

13. The compound as claimed in claim 12, wherein the useful plant comprises one or more transgenic useful plants.

14. The compound as claimed in claim 1, wherein Q is Q1.

15. The compound as claimed in claim 1, wherein Q is Q2.

16. The compound as claimed in claim 1, wherein A is N.

17. The compound as claimed in claim 1, wherein B is N.

18. The compound as claimed in claim 1, wherein A is CY.

19. The compound as claimed in claim 1, wherein B is CH.

20. The compound as claimed in claim 1, wherein R is methyl.

* * * * *